United States Patent [19]

Zaschke et al.

[11] 4,358,393
[45] Nov. 9, 1982

[54] NEMATIC LIQUID CRYSTALS OF 5-CYANO-2-[4-ACYLOXYPHENYL]-PYRIMIDINES AND MIXTURES CONTAINING THE SAME

[75] Inventors: Horst Zaschke; Dietrich Demus; Sylvia Deresch, all of Halle, German Democratic Rep.

[73] Assignee: VEB Werk für Fernsehelektronik im VEB Kombinat Mikroelektronik, Berlin, German Democratic Rep.

[21] Appl. No.: 145,060

[22] Filed: Apr. 30, 1980

[30] Foreign Application Priority Data

May 15, 1979 [DD] German Democratic Rep. ... 212876
May 15, 1979 [DD] German Democratic Rep. ... 212877

[51] Int. Cl.$^3$ .................. C09K 3/34; G02F 1/13; C07D 239/32
[52] U.S. Cl. .................. 252/299.61; 252/299.5; 252/299.63; 544/242; 544/335
[58] Field of Search .......... 252/299.5, 299.61, 299.63; 544/242, 335

[56] References Cited

U.S. PATENT DOCUMENTS

| | | | |
|---|---|---|---|
| 3,947,375 | 3/1976 | Gray et al. | 252/299.66 |
| 3,951,846 | 4/1976 | Gavrilovic | 252/299.65 |
| 3,952,046 | 4/1976 | Scherrer et al. | 252/299.66 |
| 3,997,536 | 12/1976 | Boller et al. | 252/299.61 |
| 4,062,798 | 12/1977 | Boller et al. | 252/299.61 |
| 4,112,239 | 9/1978 | DuBois et al. | 252/299.65 |
| 4,113,647 | 9/1978 | Coates et al. | 252/299.62 |
| 4,136,053 | 1/1979 | Steinstrasser | 252/299.65 |
| 4,200,580 | 4/1980 | Hsu | 252/299.61 |
| 4,229,315 | 10/1980 | Krause et al. | 252/299.63 |
| 4,256,656 | 3/1981 | Béguin et al. | 252/299.61 |
| 4,311,610 | 1/1982 | Zaschke et al. | 252/299.61 |

FOREIGN PATENT DOCUMENTS

| | | | |
|---|---|---|---|
| 2257588 | 6/1973 | Fed. Rep. of Germany | 252/299.61 |
| 2846409 | 6/1979 | Fed. Rep. of Germany | 252/299.61 |
| 2854310 | 6/1979 | Fed. Rep. of Germany | 252/299.63 |
| 105701 | 5/1974 | German Democratic Rep. | 252/299.63 |
| 132591 | 10/1978 | German Democratic Rep. | 252/299.61 |
| 139852 | 1/1980 | German Democratic Rep. | 252/299.61 |
| 143625 | 9/1980 | German Democratic Rep. | 252/299.61 |
| 54-6884 | 1/1979 | Japan | 252/299.63 |
| 54-11887 | 1/1979 | Japan | 252/299.61 |

OTHER PUBLICATIONS

Boller, A. et al.; Mol. Cryst. Liq. Cryst., vol. 42, No. 1-3, pp. 215-231 (1977).
Nash, J. A. et al., Mol. Cryst. Liq. Cryst., vol. 25, pp. 299-321 (1974).
Zaschke, H., J. Prakt. Chemie., vol. 317, No. 4, pp. 617-630 (1975).
Schubert, H. et al.; J. Prakt. Chemie, vol. 312, pp. 494-506 (1970).
Demus, D., "Nonemissive Electrooptic Displays", pp. 83-119 (1975).
Zaschke, H., Advances in Liquid Crystal Research and Applications, Bata, Lajos, Pergamon Press, Oxford, pp. 1059-1074 (1980), Proceedings of the Third Liq. Cryst. Conf. of Socialist Countries, Budapest, 27-31, Aug. 1979.

*Primary Examiner*—Teddy S. Gron
*Attorney, Agent, or Firm*—Jordan and Hamburg

[57] ABSTRACT

Nematic liquid crystals are employed in electro-optical devices for the modulation of the transmittant or incident light and for the black and white or colored rendition of numerals, symbols and pictures.

The object of the invention is the use of nematic liquid crystals having a high positive dielectric anisotropy, a low threshold and operating voltage and high clear points and a process for making these compounds.

It was found that as liquid crystals for electro-optical devices mixtures are useful which, as an essential component, contain one or several compounds from the class of 5-cyano-2-[4-acyloxyphenyl]-pyrimidines of the formula

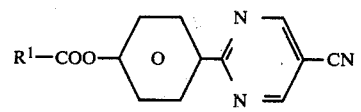

wherein
$R^1$ is

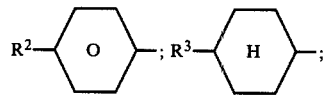

$C_5H_{11}$— or $C_nH_{2n+1}O$—
$R^2$ is $C_nH_{2n+1}$; $C_nH_{2n+1}O$; $C_nH_{2n+1}S$; F; Cl; Br; $CF_3$; $C_nH_{2n+1}COO$; $C_nH_{2n+1}OCOO$; CN; $NO_2$; $C_nH_{2n+1}NH$; or $C_nH_{2n+1}(CH_3)N$, n is 1 to 10, and
$R^3$ is $C_nH_{2n+1}$,
n is 1 to 10.

10 Claims, No Drawings

NEMATIC LIQUID CRYSTALS OF 5-CYANO-2-[4-ACYLOXYPHENYL]-PYRIMIDINES AND MIXTURES CONTAINING THE SAME

BACKGROUND OF THE INVENTION

The invention relates to nematic liquid crystals constituted by 5-cyano-2-[4-acyloxyphenyl]-pyrimidine can be used in electro-optical devices for the modulation of the transmitted or incident light and for the black and white or colored rendition of numerals, symbols and pictures.

Nematic liquid crystals having a positive dielectric anisotropy are used for electro-optical devices on the basis of the field effects, particularly of the Schadt-Helfrich effect. The compounds heretofore used which always consisted of mixtures of several compounds partially having too high a threshold and operating voltage and on the other hand too low a clear point so that they are not suited for use at higher temperatures.

An object of the invention is the use of nematic liquid crystals having a high positive dielectric anisotropy, a low threshold at operating voltage, and a high clear point, and a process for making the same.

SUMMARY OF THE INVENTION

This object is accomplished according to the invention by forming new liquid crystals and providing processes for preparing them which were previously not known. It was found that liquid crystals in the form of 5-cyano-2-[4-acyloxyphenyl]-pyrimidine of the formula

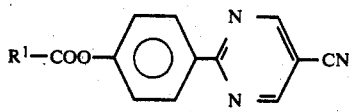

wherein

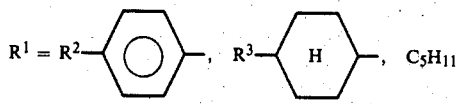

or $C_nH_{2n+1}O$-, $R^2 = C_nH_{2n+1}$, $C_nH_{2n+1}O$, $C_nH_{2n+1}S$, F, Cl, Br, $CF_3$, $C_nH_{2n+1}COO$, $C_nH_{2n+1}OCOO$, CN, $NO_2$, $C_nH_{2n+1}NH$, $C_nH_{2n+1}(CH_3)N$, and n=1 to 10 as well as $R^3 = C_nH_{2n+1}$, with n=1 to 10.

can be employed for electro-optical structural elements for the modulation of the transmitted or incident light as well as the black and white or colored rendition of numerals, symbols and pictures in the form of mixtures containing at least one compound of the invention. The advantages of the compounds of the invention are in their high dielectric anisotropy, the high clear point and the low threshold at operating voltages. An advantage is also in their black and white or colored rendition of numerals, letters or symbols in electro-optical devices.

DETAILED DESCRIPTION OF PREFERRED EMBODIMENTS

The invention will be explained as follows by way of five examples:

EXAMPLE 1

The following Table shows Examples for the 5-cyano-2-[4-acyloxyphenyl]-pyrimidines.

TABLE 1

| $R^1$ | K | | S | | N | | I |
|---|---|---|---|---|---|---|---|
| $C_5H_{11}$ | — | 107 | — | — | — | 123 | — |
| $C_4H_9O$ | ō | 121 | — | — | ō | 129 | ō |
| $C_6H_{13}O$ | ō | 83 | ō | 96 | ō | 121 | ō |
| $C_6H_{13}$–⟨O⟩– | ō | 106 | ō | 112 | ō | 249 | ō |
| $CH_3O$–⟨O⟩– | o | 224 | — | — | o | 334 | ō |
| $C_5H_{11}O$–⟨O⟩– | o | 130 | — | — | ō | 278 | ō |
| $C_5H_{11}$–⟨H⟩– | ō | 117 | ō | 192 | ō | 248 | ō |

EXAMPLE 2

A mixture of the composition

| | |
|---|---|
| 4-n-propylcyclohexanecarboxylic acid-4-cyanophenylester | 30% |
| 4-n-butylcyclohexanecarboxylic acid-4-cyanophenylester | 30% |
| 4-n-pentylcyclohexanecarboxylic acid-4-cyanophenylester | 30% |
| 5-cyano-2-[4-hexyloxycarbonyloxy-phenyl]-pyrimidine | 10% | is suitable for electro-optical structural elements of the basis of the Schadt-Helfrich effects and has the following properties:

| Melting point | 0 to 10° C. |
|---|---|
| Clear point | 73° C. |
| Threshold voltage | 1.3 V; 50 Hz |
| Operating voltage | 2.6 V |

EXAMPLE 3

Preparation of 5-cyano-2-[4-hydroxy-phenyl]pyrimidine.

50 ml abs. triethylamine, 50 ml abs. pyridine, 17.3 g (0.1 mol) 4-hydroxybenzamidine-hydrochloride and 11 g (0.1 mol) α-cyano-β-dimethylamino-acroleine are heated upon stirring for 6 hours to 80° C. Dark brown colored reaction mixture is poured on ice/concentrated $H_2SO_4$ (500 g/50 ml), the precipitate is removed by suction, washed thoroughly with water and recrystallized from methanol/activated carbon. The yield is 12.8 g (65% of the theoretical value). m.p.: 160–262 (sublimed).

EXAMPLE 4

The preparation of the 5-cyano-2-[4-acyloxy-phenyl]-pyrimidines

The preparation of these compounds is effected by reacting the 5-cyano-2-[4-hydroxy-phenyl]-pyrimidine with acid chlorides according to the modification of Einhorn or Schotten-Baumann according to the general scheme:

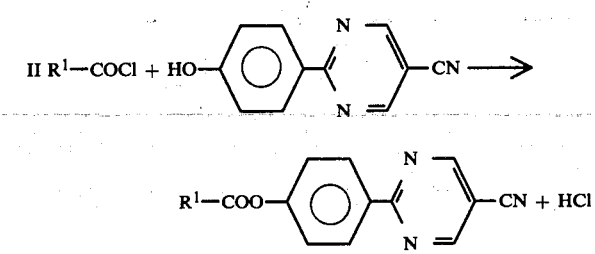

1.97 g (0.01 mol) of 5-cyano-2-[4-hydroxy-phenyl]-pyrimidine and 0.015 mol of a corresponding acid chloride are stirred into 25 ml absolute pyridine for 6 hours at room temperature whereupon the mass is heated for 5 minutes at reflux and is permitted to stand overnight.

The reaction product is poured onto ice/concentrated $H_2SO_4$ (300 g/20 ml), is taken up in ether and the ether and the ether phase is washed with 1 n KOH solution and water. Subsequently it is dried with $Na_2SO_4$, the solvent is distilled off at a rotary evaporator and the residue is recrystallized several times from n hexane. The yield is 70 to 90% of the theoretical.

EXAMPLE 5

Making of the 5-cyano-2-[4-alkyl or alkyloxy-phenyl]-pyrimidines.

This production is effected according to the general scheme I in which $R' = C_nH_{2n+1}-$ or $C_nH_{2n+1}O-$.

40 ml of absolute triethylamine, 1,1 g (0.01 mol) α-cyano-β-dimethyl-amino-acroleine and 0.01 mol substituted benzamidine-hydrochloride or the free base thereof were heated upon stirring for 6 hours to 80° C. The cooled reaction gas was poured onto 150 g ice/30 ml concentrated $H_2SO_4$, the precipitate was removed by suction, washed thoroughly with water and subsequently recrystallized several times in n-hexane. The yield was 75 to 95% of the theoretical value. Examples are found in Table 2.

TABLE 2

| R | K | | S_A | | N | | I |
|---|---|---|---|---|---|---|---|
| C_4H_9O | o | 119 | — | | o | 139 | o |
| C_5H_11O | o | 97 | o | 102.5 | o | 133 | o |
| C_6H_13O | o | 92.5 | o | 122 | o | 134.5 | o |
| C_7H_15O | o | 102 | o | 127 | o | 129 | o |
| C_4H_9 | o | 109 | — | — | (o | 101) | o |
| C_5H_11 | o | 94 | (o | 93.5) | o | 109 | o |
| C_7H_15 | o | 94 | o | 107 | — | — | o |
| C_9H_19 | o | 90 | o | 107 | — | — | o |

We claim:

1. A 5-cyano-2-[4-acyloxyphenyl]-pyrimidine of the formula

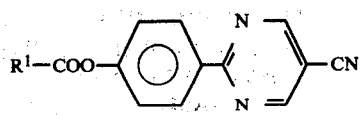

wherein $R^1$ is

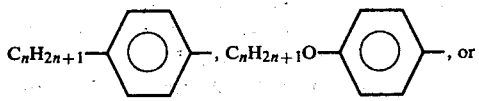

and n=1 to 10.

2. The compound of claim 1 wherein $R^1$ is

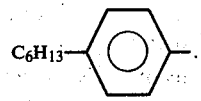

3. The compound of claim 1 wherein $R^1$ is

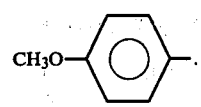

4. The compound of claim 1 wherein $R^1$ is

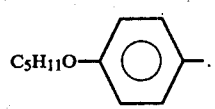

5. The compound of claim 1 wherein $R^1$ is

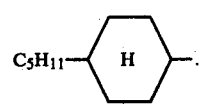

6. A nematic, liquid crystal composition comprising at least one nematic, liquid crystal compound and a compound of claim 1.

7. The composition of claim 6 comprising said at least one nematic liquid crystal compound of different structure from said compound.

8. The composition of claim 7 wherein said at least one compound of different structure is selected from the group consisting of 4-n-propylcyclohexanecarboxylic acid-4-cyanophenylester, 4-n-butylcyclohexanecarboxylic acid 4-cyanophenylester, 4-n-pentylcyclohexanecarboxylic acid 4-cyanophenylester, and mixtures thereof.

9. 5-cyano-2-(4-hexyloxycarbonyloxy phenyl) pyrimidine.

10. A nematic liquid crystal mixture composed of

| | |
|---|---|
| 4-n-propylcyclohexanecarboxylic acid-4-cyanophenylester | 30% |
| 4-n-butylcyclohexanecarboxylic acid-4-cyanophenylester | 30% |
| 4-n-pentylcyclohexanecarboxylic acid-4-cyanophenylester | 30% |
| 5-cyano-2-[4-hexyloxycarbonyloxy-phenyl]-pyrimidine | 10%. |

* * * * *